(12) United States Patent
Lu

(10) Patent No.: US 7,024,242 B2
(45) Date of Patent: Apr. 4, 2006

(54) IMPLANTABLE CARDIAC STIMULATION DEVICE WHICH RECOMMENDS ABLATION THERAPY AND METHOD

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 688 days.

(21) Appl. No.: 10/137,604

(22) Filed: May 1, 2002

(65) Prior Publication Data

US 2003/0208239 A1    Nov. 6, 2003

(51) Int. Cl.
A61B 18/18    (2006.01)
A61B 5/0464    (2006.01)

(52) U.S. Cl. ............... 607/14; 606/41; 600/515

(58) Field of Classification Search ........... 607/2–4, 607/7, 9, 14, 15, 98–99, 101–105; 600/509, 600/515, 518; 606/41
See application file for complete search history.

(56) References Cited

U.S. PATENT DOCUMENTS

| | | | |
|---|---|---|---|
| 5,713,929 A | 2/1998 | Hess et al. | ............. 607/14 |
| 5,951,593 A | 9/1999 | Lu et al. | ............. 607/14 |
| 6,431,173 B1 * | 8/2002 | Hoffmann | ............. 128/898 |
| 6,443,950 B1 * | 9/2002 | Sutton | ............. 606/41 |
| 6,671,547 B1 * | 12/2003 | Lyster et al. | ............. 607/6 |

OTHER PUBLICATIONS

Baszko, A. et al.; "Inter-Atrial Conduction Delay Identifies Patients Who Develop Atrial Fibrillation after Successful Flutter Ablation;" PACE 24:725 (Apr. 2001).

* cited by examiner

Primary Examiner—Jeffrey R. Jastrzab
Assistant Examiner—John D. Alexander

(57) ABSTRACT

An implantable cardiac stimulation device provides a stimulation therapy or an atrial ablation recommendation responsive to detection of atrial flutter of a heart. The device includes a sensing circuit that senses electrical activity of a heart and generates electrical signals representing electrical activity of the heart, an arrhythmia detector that detects atrial flutter of the heart, and a data processor that measures cardiac data responsive to the electrical signals. A therapy control responsive to the detection of atrial flutter recommends atrial ablation of the heart when the cardiac data satisfies a predetermined criteria and atrial flutter suppression when the cardiac data fails to satisfy the predetermined criteria. The device may further include a pulse generator that provides stimulation therapy to at least one atrium to terminate the atrial flutter.

14 Claims, 4 Drawing Sheets

IMPLANTABLE CARDIAC STIMULATION DEVICE WHICH RECOMMENDS ABLATION THERAPY AND METHOD

CROSS-REFERENCE TO RELATED APPLICATIONS

This application is related to copending U.S. patent application Ser. No. 10/136,916, filed May 1, 2002, titled "Implantable Cardiac Device for Restoring Inter-Chamber Synchrony and Method."

FIELD OF THE INVENTION

The present invention generally relates to an implantable cardiac stimulation device and more particularly to such a device which, responsive to detecting atrial flutter, recommends atrial ablation therapy if cardiac data satisfies a predetermined criteria.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the heart left side, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing and sensing, left ventricular pacing and sensing, or cardioversion and defibrillation. These advancements enable implantable cardiac stimulation devices to provide therapy and diagnostics not previously possible. For example, it has been demonstrated that atrial fibrillation may be terminated with the application of electrical energy between an electrode placed in the right atrium and an electrode placed in the coronary sinus adjacent the left atrium. Further, inter-chamber conduction delays during bi-chamber (both atria or both ventricles either simultaneously or in sequence) pacing may now be monitored between the right ventricle and the left ventricle and/or between the right atrium and the left atrium to determine if normal propagation of R waves and P waves, respectively, is present.

It has recently been hypothesized that dissociation between a right chamber and a corresponding left chamber may be responsible for the precipitation of tachyarrhythmias. More specifically, it has been hypothesized that long or significantly variable interventricular conduction delays or interatrial conduction delays may be prone to the development of ventricular fibrillation or atrial fibrillation, respectively.

A recent study indicated that patients with long interatrial conduction delay were likely to develop atrial fibrillation. The study further indicated that patients who had a history of previous atrial fibrillation had a 90% risk of developing atrial fibrillation after atrial flutter ablation. Atrial ablation is a well known therapy wherein cauterization, cryosurgery, diathermy, fulguration, laser or cutting is applied to an atrium to eliminate the site of origin of atrial tachycardia or to interrupt the pathway through which the atrial tachyarrhythmia travels. The study concluded that patients with a history of previous atrial fibrillation and who have long interatrial conduction delay are unlikely to benefit from atrial flutter ablation.

SUMMARY OF THE INVENTION

The present invention provides an implantable cardiac device capable of detecting an atrial flutter and then, based upon prior measured cardiac data, provides an indication whether the patient is likely to benefit from atrial flutter ablation. The present invention further provides such a device which is also capable of providing a recommendation for stimulation therapy should the prior measured data indicate that the patient would not likely benefit from atrial flutter ablation. Preferably the device includes a pulse generator for terminating the atrial flutter.

More specifically, the present invention provides an implantable cardiac device including a sensing circuit that senses electrical activity of a heart and generates electrical signals representing the electrical activity of the heart, an arrhythmia detector that detects atrial flutter of the heart, and a data processor that measures cardiac data responsive to the electrical signals. The device further includes an analyzer that analyzes the cardiac data responsive to detection of atrial flutter and that indicates atrial ablation when the cardiac data satisfies a predetermined criteria.

The device may further include a pulse generator that provides stimulation pulses to at least one atrium of the heart to terminate the atrial flutter. The analyzer may also provide a recommendation for stimulation therapy if the cardiac data fails to satisfy the predetermined criteria. Such a recommendation would be most helpful if the device is not capable of providing or is not currently programmed for providing appropriate stimulation therapy to prevent or suppress atrial flutter before its onset.

The predetermined criteria may include a lack of atrial fibrillation episodes. Accordingly, the arrhythmia detector may be further capable of detecting atrial fibrillation episodes of the heart, and the data processor may provide a recording of detected atrial fibrillation episodes for use by the analyzer.

The predetermined criteria may include normal interatrial conduction delays. Accordingly, the data processor may measure interatrial conduction delays for use by the analyzer in determining normalcy of the interatrial conduction delays. The data processor may further measure cardiac intervals corresponding to the interatrial conduction delays and the analyzer may determine normalcy of the interatrial conduction delays by determining if the interatrial conduction delays are within specified ranges in relation to the corresponding cardiac intervals.

The predetermined criteria may include non-lengthening of interatrial conduction delays. Accordingly, the data processor may measure interatrial conduction delays and the analyzer may determine if the interatrial conduction delays are lengthening.

The predetermined criteria may include stable interatrial conduction delays. Accordingly, the data processor may measure interatrial conduction delays and the analyzer may determine if the interatrial conduction delays are stable.

The present invention further provides a method of treating atrial flutter of a heart for use in an implantable cardiac device. The method includes the steps of sensing electrical activity of a heart to provide electrical signals representing the electrical activity of the heart, detecting for atrial flutter of the heart, measuring cardiac data responsive to the electrical signals, analyzing the cardiac data to determine if the data satisfies predetermined criteria, and providing an indication for atrial ablation if the cardiac data satisfies the predetermined criteria.

The method may further include the step of providing an indication for stimulation therapy to prevent or suppress the onset of atrial flutter if the cardiac data fails to satisfy the predetermined criteria.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
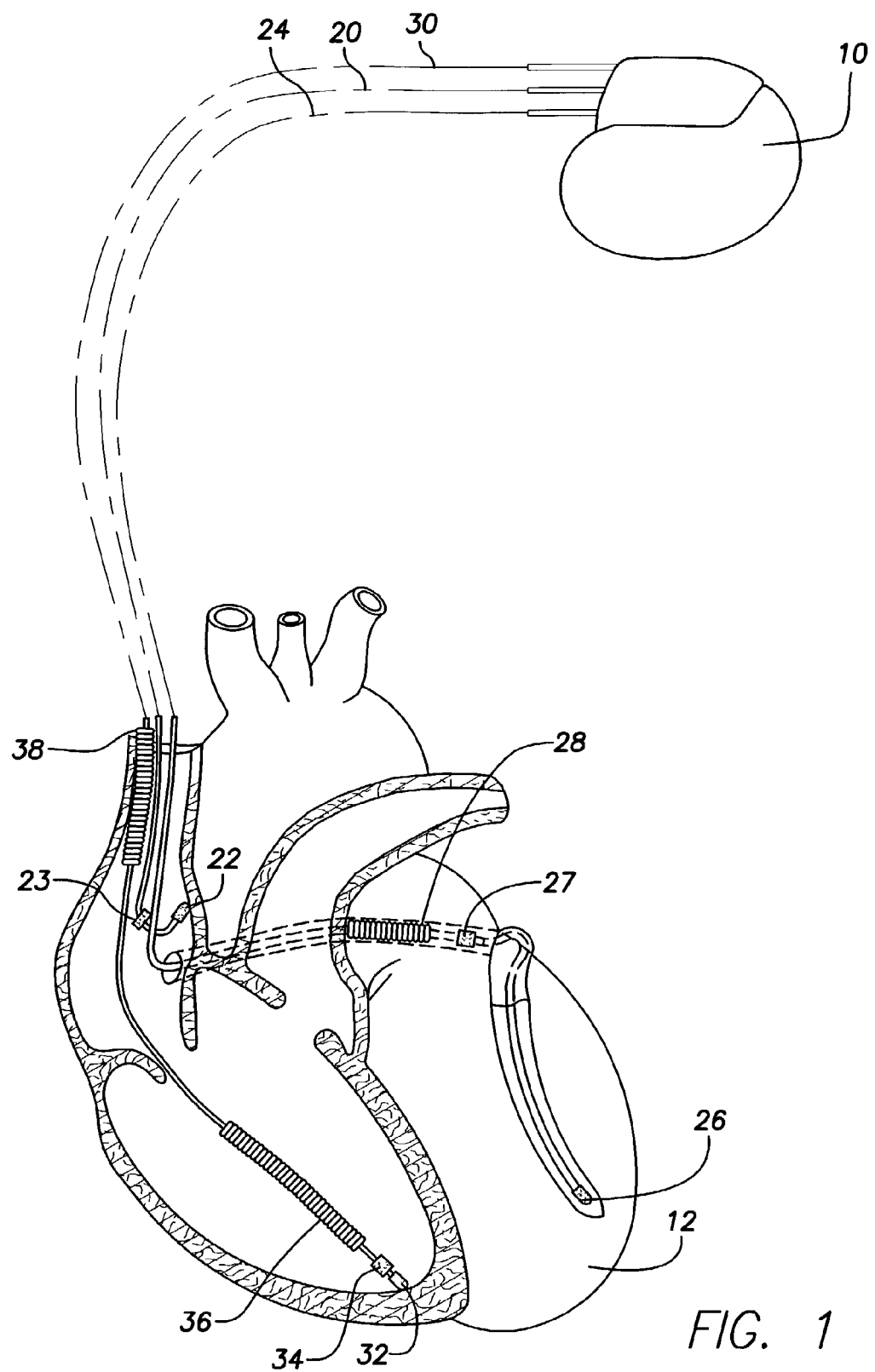
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having a right atrial tip electrode 22 and a right atrial ring electrode 23, which are implanted in the patient's right atrium.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
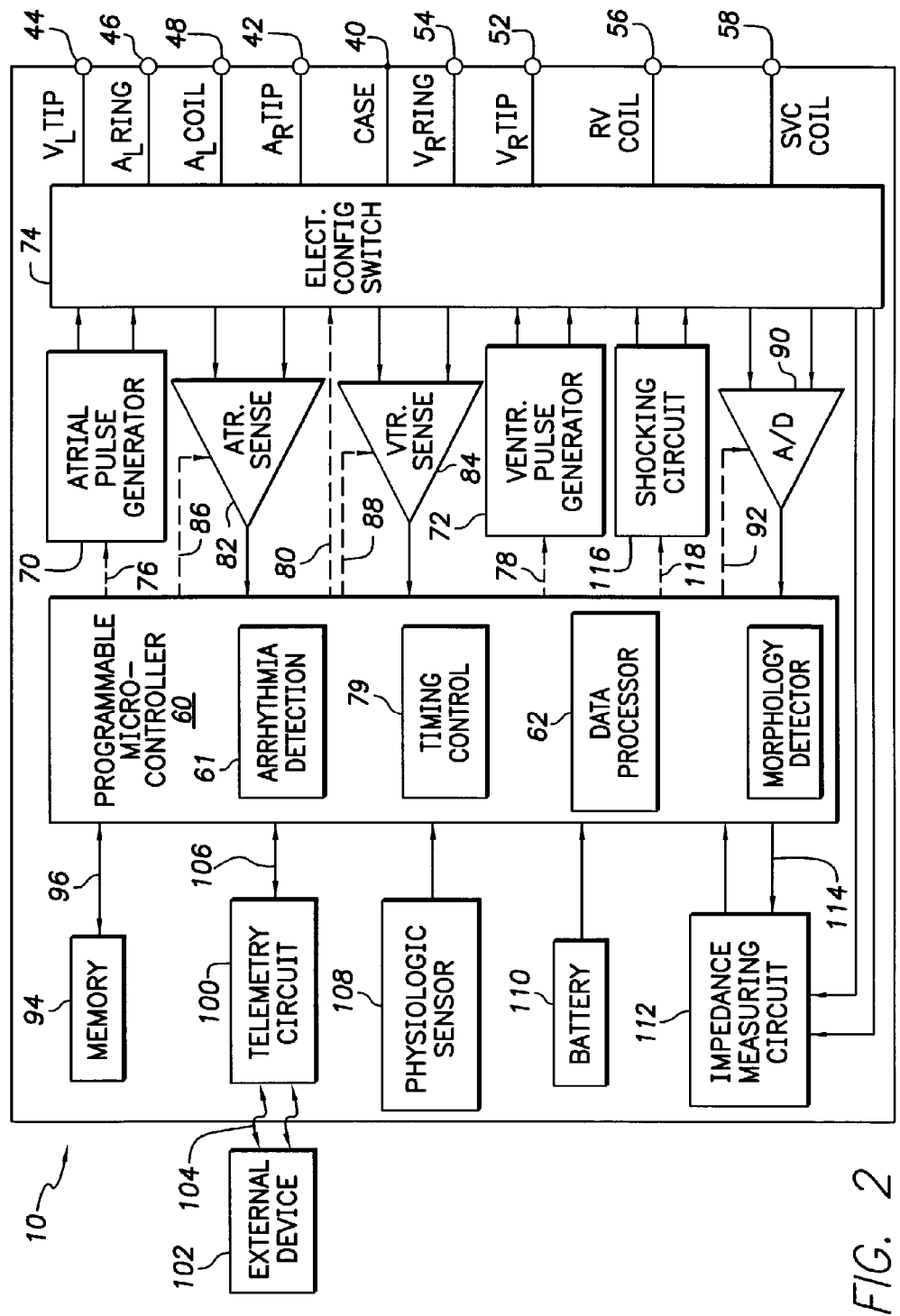
FIG. 2 is a functional block diagram of a multi-chamber implantable stimulation device embodying the present invention which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the right atrial tip electrode 22 and a right atrial ring terminal (A$_R$ RING) 43 adapted for connection to the right atrial ring electrode 23.

To achieve left chamber sensing, pacing and shocking, the connector includes at least a left ventricular tip terminal (V$_L$ TIP) 44, a left atrial ring terminal (A$_L$ RING) 46, and a left atrial shocking terminal (A$_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (V$_R$ TIP) 52, a right ventricular ring terminal (V$_R$ RING) 54, a right ventricular shocking terminal (R$_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 includes an arrhythmia detector 61 which utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, atrial flutter and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the exemplary implantable cardiac device 10 has been generally described, the following description of the device is more particularly directed to those aspects of the device 10 which enable the device to implement the therapy contemplated by the present invention. As previously described, the present invention is broadly directed to atrial flutter therapy. More particularly, if the device 10 detects atrial flutter, it then analyzes prestored cardiac data to determine if the data satisfies predetermined criteria to identify the patient as one who would most likely benefit from atrial ablation. If the data satisfies the predetermined criteria, the device then provides a recommendation of atrial ablation. If the data fails to satisfy the predetermined criteria, the device recommends suppression therapy. Either before or after providing the recommendation for either atrial ablation or suppression therapy, the device preferably then proceeds to stimulate the heart with antitachycardia pacing to terminate the atrial flutter so that the patient is not left in that condition. The suppression therapy applied or recommended may include dynamic atrial overdrive pacing wherein the heart is paced at a rate slightly higher than the intrinsic rate. Such pacing is described, for example, in copending U.S. application Ser. No. 09/471,788, filed Dec. 23, 1999, for Methods and Apparatus for Overdrive Pacing Heart Tissue Using an Implantable Cardiac Stimulation Device and U.S. application Ser. No. 10/017,836, filed Dec. 12, 2001, for Dynamic Control of Overdrive Pacing Based on Degree of Randomness Within Heart Rate, which applications are incorporated herein by reference. Such pacing is also described, for example, in U.S. Pat. No. 5,713,929 which issued on Feb. 3, 1998 and which is also incorporated herein by reference.

In a healthy heart, an activation of the right atrium (a right atrial P wave) is generally followed by a left atrial activation (a left atrial P wave) within a normal interatrial conduction delay interval of about, for example, 10 to 50 milliseconds. Non-beneficial atrial ablation may be indicated by abnormal interatrial conduction delays with respect to cardiac rate, an abrupt or gradual increase in the inter-atrial delay, instability of the inter-atrial delay or a previous history of atrial fibrillation. Any one of these conditions can be the basis for a determination that atrial ablation would most likely not be beneficial.

In view of the above, the present invention contemplates the sensing of intracardiac signals of the heart and generating electrical signals representing the electrical activity or conduction from the right to the left atria or vice versa of the heart. Cardiac data is measured from the electrical signals and stored. If atrial flutter is detected it is then determined if the data satisfies the predetermined criteria. If it does, the device provides an indication that atrial ablation would likely be beneficial. The predetermined criteria preferably includes the lack of atrial fibrillation episodes, normal interatrial delays, non-lengthening interatrial delays, and stable interatrial delays. For determining interatrial conduction delays, even markers may be utilized in a manner well known in the art.

Returning now to FIG. 2, and the embodiment illustrated, the electrogram signals representing the electrical activity of the right and left atria are generated by the data acquisition system 90. Preferably, for interatrial monitoring, the data acquisition system generates at least two electrograms. The right atrial electrodes 22 and 23 generate a right atrial electrogram and the left atrial electrodes 27 and 28 generate a left atrial electrogram. In addition, the right ventricular electrodes 32 and 34 generate a ventricular electrogram.

The electrogram signals thus generated are used by the microprocessor 60 to provide cardiac data. To that end, the microprocessor 60 includes a data processor 62. The data processor 62, for each cardiac cycle, uses the ventricular electrogram to determine a cardiac interval from ventricular event markers, for example. It also uses the atrial electrograms to determine an interatrial conduction delay from atrial event markers, for example. This data is determined each cardiac cycle for both intrinsic rhythms and paced beats. Each interatrial conduction delay is then stored in a rate bin corresponding to the associated cardiac interval. The bins may be established, for example, in the memory 94. Further, any episode of atrial fibrillation detected by the arrhythmia detector 61 is also recorded in memory 94.

The microprocessor 60 further includes a morphology detector 64. The detector 64, of a type well known in the art, may be employed to confirm detection of a stable atrial flutter. As is well known, morphology may be used to confirm that a flutter is from the same atrial scarring tissue. Hence, by comparing the morphology of a detected atrial flutter to a known morphology for atrial flutter heart activity, detection of a stable atrial flutter may be confirmed.

In accordance with this embodiment, the atrial flutter is terminated by the pulse generator 72 applying the stimulation pulses to one or both atria. The pulse generator 72 times delivery of the stimulation pulses under control of the timing control 79. That timing control may determine the delivery time of a single stimulation pulse or preferably cause the pulse generator 72 to stimulate one or both of the atria in an antitachycardia pacing mode.

Figure 3:
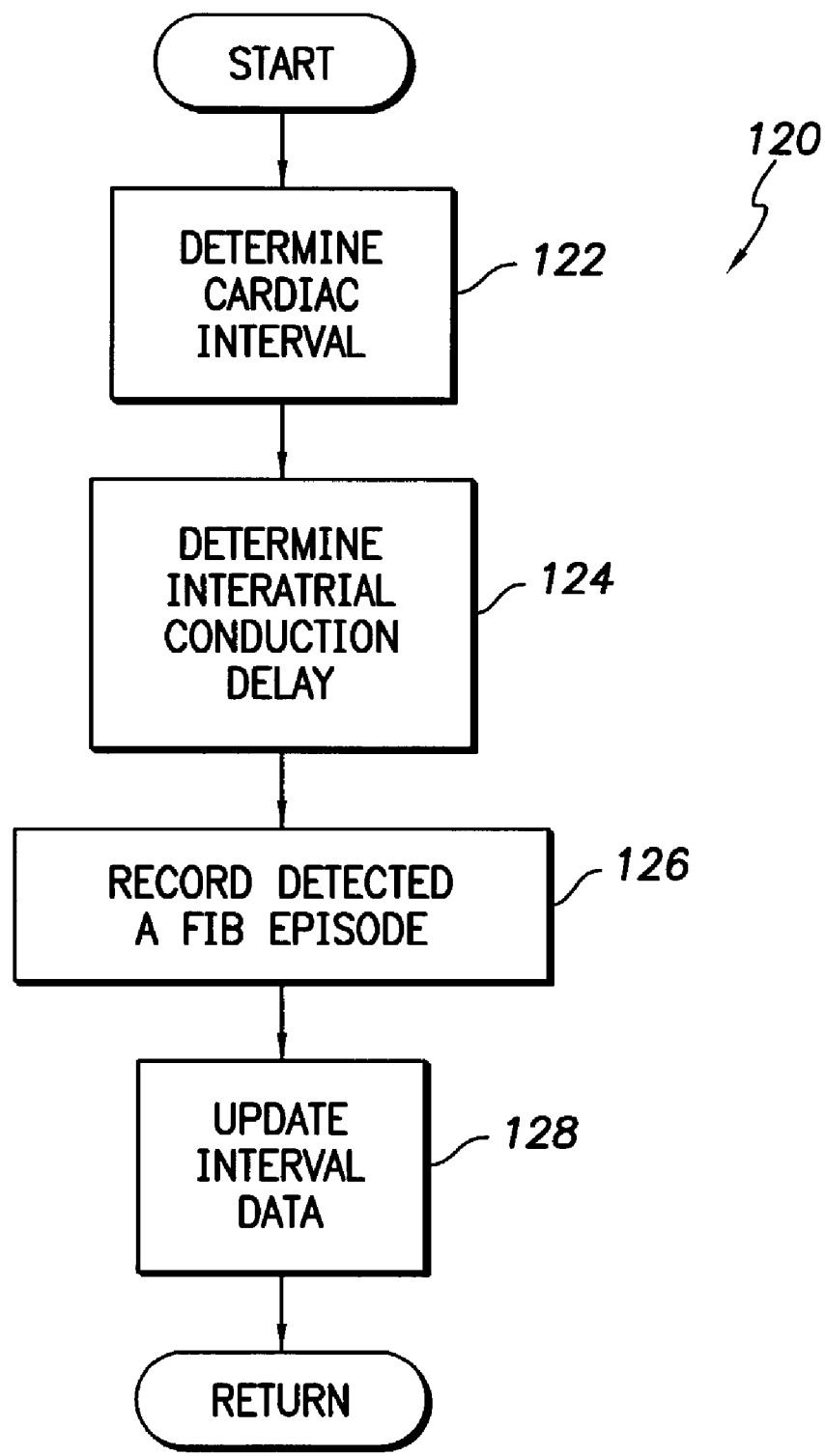
FIG. 3 is a flow chart describing cardiac data generating and recording in accordance with an embodiment of the present invention.

In FIG. 3, a flow chart 120 is shown describing an overview of the manner in which cardiac data is determined by the device 10 after each cardiac cycle in accordance with an embodiment of the present invention. In this flow chart, and the flow chart of FIG. 4 described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 is repeated after each cardiac cycle, whether intrinsic or paced, and initiates at activity block 122 with the determination of a last cardiac interval. The cardiac interval may be determined using consecutive R wave event markers and calculating or timing the time between the markers in a manner known in the art.

The process then proceeds to activity block 124. Here, the interatrial conduction delay is determined for the cardiac cycle just completed. Again, atrial event markers may be used. More specifically the time interval between the right atrial P wave and the left atrial P wave is determined. Since interatrial conduction intervals may be slightly different for paced and intrinsic beats, they should preferably be stored separately for determining interatrial conduction stability.

Next, the process advances to activity block 126. Here, any detected episode of atrial fibrillation is recorded in the memory 94. The recording may include a time stamp so that the times of the episodes may be determined if desired.

Lastly, the process of FIG. 3 advances to activity block 128. Here, the interatrial conduction delay is stored in its associated rate bin. The interatrial conduction delay may also be stored in a further and separate memory location or time stamped to permit interatrial conduction delay trends to be determined as described subsequently. The process then returns and will reinitiate after completion of the next cardiac cycle.

Figure 4:
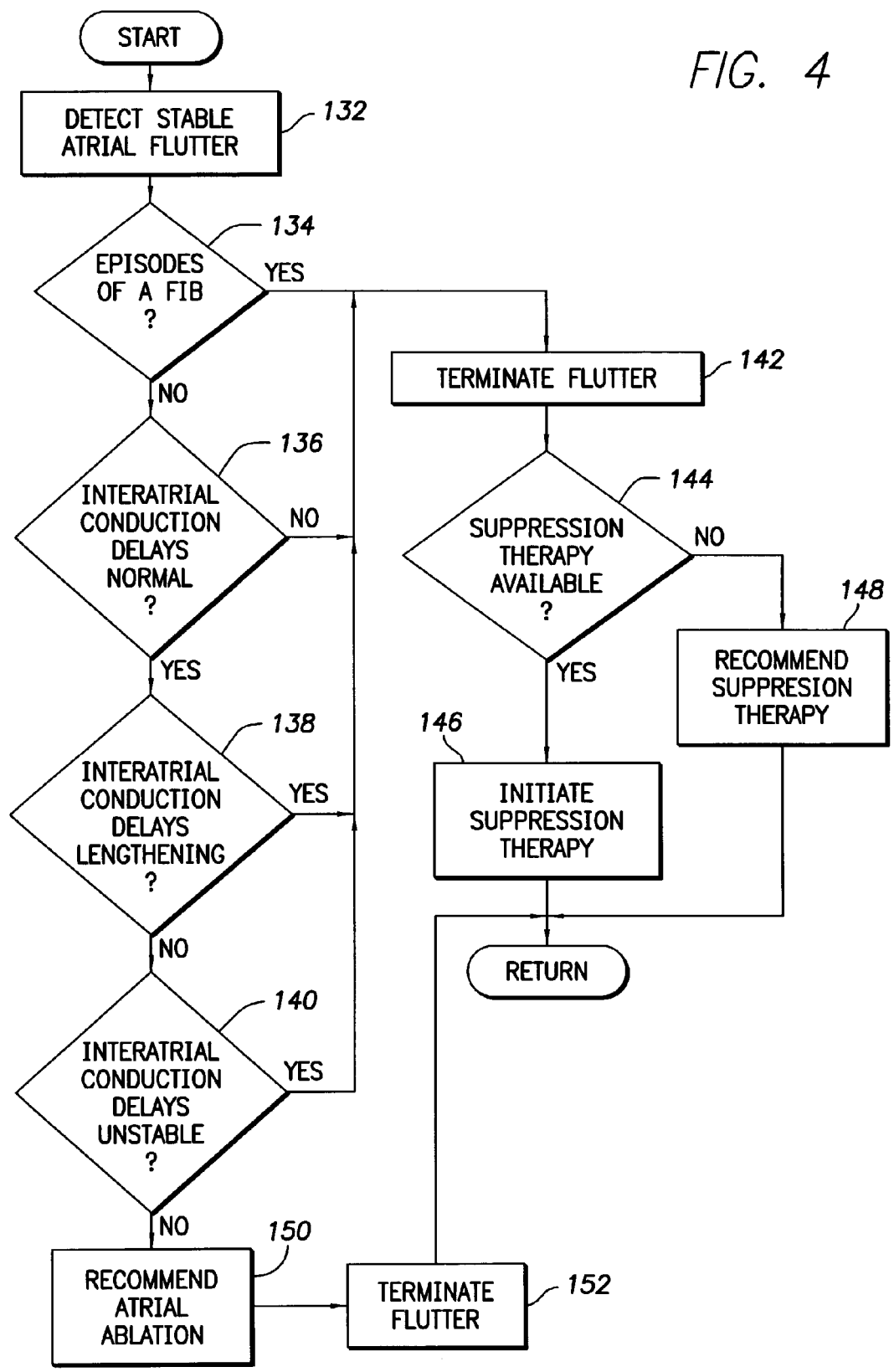
FIG. 4 is a flow chart describing an overview of atrial therapy in accordance with an embodiment of the present invention.

FIG. 4 is a flow diagram 130 describing an atrial flutter therapy embodying the present invention. The process initiates at an activity block 132. Here, a stable atrial flutter is detected by the arrhythmia detector 61. The atrial flutter may be detected by determining when the atrial rate remains within an atrial flutter zone and that the rate has low variability. The stable atrial flutter may further be confirmed by comparing the morphology of the atrial activity with a known morphology. Once confirmed to be sourced by the same scarring tissue, the process then advances to determine if atrial ablation would be of benefit to treat the stable atrial flutter.

During this phase of the therapy, the cardiac data generated as described in FIG. 3 is analyzed to determine if it satisfies predetermined criteria. That criteria, in accordance with this embodiment includes lack of atrial fibrillation episodes, normal interatrial conduction delays, non-lengthening interatrial conduction delays, and stable interatrial condition delays.

As shown in decision block 134, it is first determined if there have been detected atrial fibrillation episodes. If at least one atrial fibrillation episode has been detected and recorded, the process immediately advances to atrial flutter termination and suppression therapy beginning with activity block 142.

In activity block 142, the device 10 stimulates at least one of the atria to terminate the atrial flutter. The stimulation preferably takes the form of atrial antitachycardia pacing of one or both of the atria. Such pacing is well known in the art. If such pacing fails to terminate the atrial flutter, a single cardioverting/defibrillating shock may then be delivered to the atria as previously described. Once the atrial flutter is terminated, the process returns.

The atrial flutter termination and suppression therapy then advances to decision block 144 where it is determined if the device is capable of providing atrial flutter prevention or suppression therapy such as the dynamic atrial overdrive pacing previously described. If the device is capable of providing such therapy, the process advances to activity block 146 wherein atrial flutter suppression therapy is initiated. If such therapy is not available with the device, then the process advances to activity block 148 wherein a recommendation for such therapy is formulated and either transmitted to the physician or stored in the memory 94 for later transmission to the physician. Following activity blocks 146 and 148, the process returns.

If it is determined in decision block 134 that there have not been any detected and recorded atrial fibrillation episodes, the process then advances to decision block 136. Here it is determined if the interatrial conduction delays have been normal. More specifically, it is determined if the interatrial conduction delays for the different rate bins are within specified ranges. If the interatrial conduction delays are not normal, the process then immediately advances to activity block 142 to begin atrial flutter termination and suppression therapy as previously described. If they are normal, however, the process then advances to decision block 138 to determine if the interatrial conduction delays have been lengthening. Here, successive interatrial conduction delays are compared. If they have been lengthening, the process advances to activity block 142 to begin atrial flutter termination and suppression therapy. If the interatrial conduction delays have not been lengthening, the process then advances to decision block 140. Here it is determined if the interatrial conduction delays have been unstable. The outcome is positive, for example, if the variability in interatrial delay over a last number of cycles, for example 15–60 cycles, is greater than a certain number, such as 15–25 milliseconds. If it is, the interatrial conduction delays are considered unstable and the process immediately advances to activity block 142 to begin atrial flutter termination and suppression therapy. However, if the interatrial conduction delays are found to be stable, all of the predetermined criteria have been satisfied and the process advances to activity block 150 to recommend atrial ablation therapy. Here the recommendation may be the setting of a flag. Alternatively the recommendation may be in the form of a message to that effect to be displayed on the programmer 102 during the patient's next follow-up visit or the message may be transmitted remotely to the physician. Once the recommendation for atrial ablation is complete, the process advances to activity block 152 to terminate the atrial flutter as previously described with respect to activity block 142.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac device comprising:
a sensing circuit that senses electrical activity of a heart and generates electrical signals representing the electrical activity of the heart;
an arrhythmia detector that receives the electrical signals from the sensing circuit and that detects atrial flutter of the heart;
a data processor that provides cardiac data responsive to receipt of the electrical signals and measures interatrial conduction delays for the provided cardiac data; and
an analyzer, connected to the data processor, that analyzes the interatrial conduction delays responsive to detection of atrial flutter and that indicates atrial ablation when the interatrial conduction delays are stable.

2. The device of claim 1 wherein the arrhythmia detector further detects atrial fibrillation episodes of the heart, and wherein the data processor provides a recording of detected atrial fibrillation episodes and wherein the analyzer indicates atrial ablation if there has been a lack of detected atrial fibrillation episodes.

3. The device of claim 1 wherein the analyzer indicates atrial ablation if the interatrial conduction delays are normal.

4. The device of claim 3 wherein the data processor further measures cardiac intervals corresponding to the interatrial conduction delays and the analyzer determines normalcy of the interatrial conduction delays by determining if the interatrial conduction delays are within specified ranges in relation to the corresponding cardiac intervals.

5. The device of claim 1 wherein the analyzer indicates atrial ablation if the interatrial conduction delays are non-lengthening as a function of time, and wherein the analyzer determines if the interatrial conduction delays are lengthening.

6. An implantable cardiac device comprising:
sensing means for sensing electrical activity of a heart and generating electrical signals representing the electrical activity of the heart;
arrhythmia detecting means for detecting atrial flutter of the heart;
data processing means for providing cardiac data responsive to the electrical signals and for measuring an interatrial conduction delay for the cardiac data; and
analyzing means for analyzing the the interatrial conduction delays responsive to detection of atrial flutter to determine if the interatrial conduction delays are stable and indicating atrial ablation when the interatrial conduction delays are stable.

7. The device of claim 6 wherein the arrhythmia detecting means includes atrial fibrillation detecting means for detecting atrial fibrillation episodes of the heart, and wherein the data processing means includes means for recording detected atrial fibrillation episodes and the analyzing means indicates atrial ablation if there has been a lack of detected atrial fibrillation episodes.

8. The device of claim 6 wherein analyzing means further analyzes the interatrial conduction delays to determine if the interatrial conduction delays are normal.

9. The device of claim 8 wherein the data processing means includes means for measuring cardiac intervals corresponding to the interatrial conduction delays and wherein the analyzing means determines normalcy of the interatrial conduction delays by determining if the interatrial conduction delays are within specified ranges in relation to the corresponding cardiac intervals.

10. The device of claim 6 wherein analyzing means further analyzes the interatrial conduction delays to determine if the interatrial conduction delays are lengthening as a function of time.

11. A method of treating atrial flutter of a heart for use in an implantable cardiac device, the method comprising:
sensing electrical activity of a heart to provide electrical signals representing the electrical activity of the heart;
monitoring for atrial flutter of the heart;
measuring cardiac data responsive to the electrical signals;
analyzing the cardiac data to determine interatrial conduction delays and cardiac intervals corresponding to the interatrial conduction delays; and
providing an indication for atrial ablation in response to detection of atrial flutter if the interatrial conduction delays are within specified ranges in relation to the corresponding cardiac intervals.

12. The method of claim 11 wherein the method includes the further step of monitoring for atrial fibrillation episodes of the heart, and wherein the method further includes the step of recording occurrences of detected atrial fibrillation episodes and wherein providing an indication for atrial ablation further includes providing an indication for atrial ablation if there is a lack of recorded occurrences of atrial fibrillation episodes.

13. The method of claim 11 wherein analyzing the cardiac data to determine interatrial conduction delays includes analyzing the interatrial conduction delays to determine if the interatrial conduction delays are lengthening as a function of time and wherein providing an indication for atrial ablation includes providing an indication for atrial ablation if the interatrial conduction delays are not lengthening as a function of time.

14. The method of claim 11 wherein the analyzing step includes the step of determining if the interatrial conduction delays are stable and wherein providing an indication for atrial ablation includes providing an indication for atrial ablation if the interatrial conduction delays are stable.

* * * * *